United States Patent
Klutts

(10) Patent No.: US 9,918,867 B2
(45) Date of Patent: Mar. 20, 2018

(54) ORTHOPEDIC SUPPORT PAD ASSEMBLY AND METHOD FOR PROVIDING PERMANENT RELIEF ZONES

(71) Applicant: OSSUR HF, Reykjavik (IS)

(72) Inventor: Zachariah J. Klutts, Irvine, CA (US)

(73) Assignee: OSSUR HF, Reykjavik (IS)

( * ) Notice: Subject to any disclaimer, the term of this patent is extended or adjusted under 35 U.S.C. 154(b) by 359 days.

(21) Appl. No.: 14/734,169

(22) Filed: Jun. 9, 2015

(65) Prior Publication Data
US 2015/0351949 A1    Dec. 10, 2015

Related U.S. Application Data

(60) Provisional application No. 62/009,463, filed on Jun. 9, 2014.

(51) Int. Cl.
*A61F 5/30* (2006.01)

(52) U.S. Cl.
CPC ........... *A61F 5/30* (2013.01); *Y10T 156/1052* (2015.01)

(58) Field of Classification Search
CPC ........ A61F 5/30; A61F 5/0585; A61F 5/0111; A61F 13/04; A61F 5/01; A61F 5/0118; Y10T 156/1052
See application file for complete search history.

(56) References Cited

U.S. PATENT DOCUMENTS

| 975,576 A | 11/1910 | Sexton |
|---|---|---|
| 1,473,392 A | 11/1923 | Buckley |
| 2,868,191 A | 1/1959 | Juhasz |
| 2,885,797 A | 5/1959 | Chrencik |
| 2,909,854 A | 10/1959 | Edelstein |
| 2,913,837 A | 11/1959 | Geuder |
| 2,979,836 A | 4/1961 | Scholl |
| 3,548,420 A | 12/1970 | Spence |
| 3,859,740 A | 1/1975 | Kemp |
| 4,095,353 A | 6/1978 | Foldes |
| 4,100,686 A | 7/1978 | Sgarlato et al. |

(Continued)

FOREIGN PATENT DOCUMENTS

| FR | 2 681 516 A1 | 3/1993 |
|---|---|---|
| WO | 93/13685 A1 | 7/1993 |

(Continued)

OTHER PUBLICATIONS

International Search Report from corresponding PCT Application No. PCT/US2015/034804, dated Mar. 15, 2016.

*Primary Examiner* — Ophelia A Hawthorne

(74) *Attorney, Agent, or Firm* — Workman Nydegger

(57) ABSTRACT

A pad assembly comprises a padding defining first and second surfaces, and includes a first layer being resilient and accessible from the first surface and a second layer being resilient and underlying and secured to the first layer. The first and second removable sections are formed from at least one of the first and second layers and are arranged in a pattern and separated by edge clearances. Each of the first and second removable sections is tearable from the padding such that a residual portion of the removable section remains when at least one of the first and second removable sections is removed from the padding. The pad assembly may include a strap, and a substantially rigid or rigid shell connecting to the padding and strap.

20 Claims, 2 Drawing Sheets

(56) References Cited

U.S. PATENT DOCUMENTS

| | | |
|---|---|---|
| 4,408,402 A | 10/1983 | Looney |
| 4,571,853 A | 2/1986 | Medrano |
| 4,598,484 A | 7/1986 | Ma |
| 4,608,768 A | 9/1986 | Cavanagh |
| 4,633,598 A | 1/1987 | Moronaga et al. |
| 4,689,898 A | 9/1987 | Fahey |
| 4,727,661 A | 3/1988 | Kuhn |
| 4,793,078 A | 12/1988 | Andrews |
| 4,869,001 A | 9/1989 | Brown |
| 4,893,418 A | 1/1990 | Ogden |
| 5,078,128 A | 1/1992 | Grim et al. |
| 5,154,682 A | 10/1992 | Kellerman |
| 5,197,942 A | 3/1993 | Brady |
| 5,329,705 A | 7/1994 | Grim et al. |
| 5,438,768 A | 8/1995 | Bauerfeind |
| 5,761,834 A * | 6/1998 | Grim ............... A43B 1/0009 36/110 |
| 5,768,803 A | 6/1998 | Levy |
| 5,782,780 A | 7/1998 | Mason et al. |
| 5,807,294 A | 9/1998 | Cawley et al. |
| 5,853,380 A * | 12/1998 | Miller ............... A61F 5/0111 602/23 |
| 6,394,971 B1 * | 5/2002 | Slautterback ....... A61F 5/0111 602/23 |
| 6,892,734 B1 | 5/2005 | Schleicher et al. |
| RE40,363 E | 6/2008 | Grim et al. |
| 7,485,103 B2 | 2/2009 | Mason et al. |
| 7,713,225 B2 | 5/2010 | Ingimundarson et al. |
| 8,945,031 B2 | 2/2015 | Cardinali |
| 2006/0143807 A1 | 7/2006 | Udelhofen et al. |
| 2006/0155229 A1 | 7/2006 | Ceriani et al. |
| 2006/0155232 A1 | 7/2006 | Ceriani |
| 2009/0049712 A1 | 2/2009 | Steszyn et al. |
| 2012/0016283 A1 | 1/2012 | Hollister et al. |
| 2014/0058303 A1 | 2/2014 | Cardinali |

FOREIGN PATENT DOCUMENTS

| | | |
|---|---|---|
| WO | 2010/071170 A1 | 6/2010 |
| WO | 2011051062 A1 | 5/2011 |

* cited by examiner

ORTHOPEDIC SUPPORT PAD ASSEMBLY
AND METHOD FOR PROVIDING
PERMANENT RELIEF ZONES

FIELD OF THE DISCLOSURE

The present disclosure relates to orthopedic devices, and more particularly to a conformable support pad assembly to provide permanent areas of pressure relief to the surface of an appendage in a low-cost and efficient manner.

BACKGROUND

Support pads are used in a wide variety of applications to provide cushioned support to an injured or otherwise sensitive bodily appendage. Such pads have the dual purpose of (1) providing orthopedic support to the appendage and (2) protecting the appendage from further injury or damage resulting from contact with a foreign object or hard surface.

One common use of a support pad is a cushioned pad in specialized bracing, supports or footwear such as soft boots or patient walkers. These pads employ a soft, resilient material, such as foam, to provide cushioned support of a sensitive or damaged foot.

A particular problem arises when it becomes necessary to provide uneven support across the outer surface of an appendage. Some bracing requires padding about a knee recently operated on with incision sites including sutures. While support is required for the brace, it is difficult to adapt and place pads over sensitive areas of a user's skin and incision sites. Complications may arise when it is desired to secure pads in combination with straps and bracing components such as shells.

In another example, an ulcerated appendage, often found in diabetic patients, requires pressure relief to the ulcerated area to allow healing. It is desirable to have a pad to apply cushioned support to the appendage, while refraining from supporting the afflicted area. For diabetic patients, the feet are commonly beset with such ulcerations, and it is therefore desirable to provide a cushioned support sole for a shoe or walker capable of providing zones of pressure relief.

Many solutions exist for providing pressure relief in padding, and such examples include padding having removable resilient inserts in a padding assembly relating to orthopedic devices. An example is found in U.S. Pat. RE40,363 describing removable sections held in place by pressure sensitive adhesive or hooks and loop type securing material to permit removal and replacement of the sections. The removable sections have a grid like configuration, and may cover most or substantially all of the inner padding, or may cover selected important areas corresponding to a user's anatomy. The removable sections may have various densities so a user may arrange denser sections to provide additional cushioning in selected areas of the padding.

Another example is found in U.S. patent application publication 2014/0058303 which describes a similar padding assembly found in U.S. Pat. RE 40,363 including removable sections that are reconfigurable to provide areas of pressure relief or removable sections that maintain permanent areas of pressure relief with varying heights.

With the above examples, they define complicated structures that result in expensive padding assemblies including various layers, and structures enabling reconfiguration of the removable sections. Because the bracing or support may be only temporary, especially while a user is healing, it is often unnecessary to provide a user an expensive padding assembly. Rather, it is important to provide a padding assembly that does not significantly add to the cost of an orthopedic device, while still achieving the intent of enabling pressure relief.

The above examples are described in combination with fixed structures of an orthopedic device, such as an orthopedic leg walker in U.S. Pat. RE40,363 or cuffs in a post-operative knee brace in U.S. patent application publication 2014/0058303. Instances arise in orthopedic devices requiring adaptability of a strap and movability of a shell for combination with a padding assembly. The known examples lack the versatility of a padding assembly including a rigid or substantially rigid shell adjustable with the padding itself.

From an overall standpoint, a principal object of the disclosure is to provide a comfortable padding assembly that may conveniently be placed over a user's anatomy and modified to enable pressure relief over areas of the user's anatomy. Another object is to furnish a padding assembly that includes disposable and replaceable padding for use during treatment.

SUMMARY

Various embodiments of the disclosure relate to a pad assembly arranged in a low-cost manner readily adaptable to a variety of user anatomies and needs. The pad assembly may be employed with padding and a rigid or semi-rigid shell detachable from the padding, and may be used in combination with a strap for securing against various user anatomies and appendages.

The padding defines outer and inner surfaces, with the inner surface adapted to be placed against skin of a user. A first resilient layer is accessible from the inner surface and a second resilient layer underlies and is laminated to the first layer. The padding defines at least first and second removable sections arranged in a pattern and separated by edge clearances. The first and second removable sections are arranged to be torn away from the padding.

In a first embodiment, the first layer is stripped away from the second layer, leaving a residual portion of the first layer on the padding and secured to the second layer. This may be achieved by bonding or lamination technique used to secure the first and second layers, or the selection of the materials used to form the first and second layers.

In a second embodiment, the second layer is selected from a material weaker than a material forming the first layer, and a portion of the second layer is torn with the removable section so the removable section is substantially or entirely removed from the padding, and a portion of the second layer is stripped away along with the removable portion from the remainder of the second layer. The second layer serves as a buffer between an outer surface and the removable portion, and is a weak point or section away from any wound with the depth of the removable section sufficiently sized deep to prevent contact at the pressure relief area or void created by removal of the removable section.

The residual portion of the second layer remaining after the removable portion is taken away and is advantageous in that while a pressure relief area is formed by removal of the removable section, the residual portion remains and preserves structural integrity of the padding along the outer surface. The padding can maintain sufficient structural integrity even though the removable section is removed from the padding without the necessity of a complicated and costly padding structure.

The clearance between the residual portion and the outer surface will normally provide enough distance so a pressure relief area can be formed. The ability to assure complete or near complete removal of the first layer with the removable section assures a sufficiently deep pressure relief area. The edge clearances preferably extend through an entire thickness of the first layer but preferably extend short of the second layer, although the disclosure does not limit such depth of the edge clearances, and they may extend into the second layer.

According to an embodiment, the first and second layers are flame laminated to one another to assure both a chemical and mechanical body between the two layers. Flame lamination is a process used to produce laminates by bonding over an open flame. The exposure to the flame creates a thin layer of molten polymer between the two layers. For example, the first layer is brought into contact with the secondary layer under pressure to develop a bond between two surfaces as the interface between the two layers is molten and the interface comprises a blend of material from both the first and second layers.

Due to the strong bond between the first and second layers, and the greater resiliency of the first layer compared to the second layer, material of the second layer will tear away with the removable section, preferably underneath the blended interface brought by flame lamination and a distance into the second layer, to assure complete removal of the first layer at the removable portion.

In alternative embodiments, the first and second layers may be bonded by other means such as solvent-based adhesive lamination, thermoplastic adhesive lamination, solvent and water-based coating, heat sealing, and other known methods to assure a bond between the first and second layers.

The removable sections are permanently removable from the padding, and the padding is disposable after use. Because of the simplicity of the structure of the padding, it is cost-effective to replace the padding with clean padding rather reconfigure the padding with the removable sections after sensitive areas corresponding to the pressure relief zones are healed. During treatment, rather than reconfigure the padding, which may be damaged, dirty and deteriorated, a user may replace the padding with new padding having different pressure relief areas. The padding can be replaced with padding without removable sections and the edge cuts, or an orthopedic device can be provided with a plurality of padding, both those including removable sections and those without removable sections. Alternatively, different pad assemblies may be provided with padding constructed from materials having different properties such as the first layer having variously defined stiffness, porosity, water retention or resistant properties, compression, resiliency, flexibility, etc.

From a manufacturing standpoint, the basic padding can be constructed and selectively die cut with edge clearances, however less waste is created since the basic padding can be used with or without edge clearances and the removable sections. A special structure, as taught in the prior art, is unnecessary, rather a basic structure whereby a first resilient material leaving a residual portion bonded to a second resilient material is required.

The padding assembly may further include a strap defining surface material, and a substantially rigid or rigid shell defining an inner fastener on an inner surface removably securable to the second surface of the padding, and an outer fastener on an outer surface removably securable to the surface material of the strap. The padding and the shell may each define a similar profile, with the profile of the padding preferably having a dimension larger than the profile of the shell. The inner and outer fasteners of the shell may be defined as integrally formed hook elements created from a same material forming the shell. The shell may define a three-dimensional shape defined by a V-shape cross-section including a central bend, and the padding preferably conforms to the three-dimensional shape of the shell.

The padding may define an upper portion having a wider width than the lower portion, and the first and second removable sections may be defined in the upper portion of the padding. The padding may have a periphery arranged for trimming and modification, and due to the construction, the padding may be provided in an oversized manner without materially adding significantly to the cost the padding and allowing for removal and waste.

The first layer of the padding is preferably formed from a first foam, such as an EVA, and the second layer of the padding is formed from a second foam, such as polyethylene. The first foam preferably has greater density or resiliency than the first foam to assure that the residual portion remains rather than a portion of the second layer stripping away when the removable section is removed. The first layer preferably has a thickness at least double the thickness of the second layer to assure a sufficient depth of the pressure relief area(s). The entire first layer is preferably bonded and/or laminated over the entire second layer. The residual portion of the first layer may extend over an entirety of a portion of the second layer underlying from which the removable section is removed.

The padding may include an outer layer bonded on the second layer and formed from a hook-receivable material. The thickness of the outer layer is preferably thin such that it has a thickness substantially less than a thickness of the second layer, and the outer layer defines the outer surface of the padding.

The padding may also include an inner layer bonded on the first layer and formed from a compact fabric napped and felted for a smooth surface. The inner layer preferably defines an inner surface of the padding and has a thickness substantially less than a thickness of the first layer. The inner layer is provided as a skin interface and is preferably not intended to provide any structural strength to the first layer.

A method for forming a pad assembly enabling formation of permanent pressure relief areas includes laminating and/ or bonding a first foam layer onto a second foam layer, die cutting a plurality of removable sections through a thickness of the first foam layer by forming a plurality of edge clearances between each of the removable sections. The method may include removing at least one of the plurality of removable sections corresponding to a sensitive area of a user, wherein a residual portion of the first layer remains on the second layer after the at least one removable section is removed from the pad assembly.

In a variation of the method, the first and second foam layers are flame laminated to one another, wherein the first foam layer is passed through a controlled flame changing the surface of the foam to a molten state. The second foam layer is then brought into direct contact with the molten foam under controlled tension and pressure. As the molten foam rapidly cools at the interface between the first and second foam layers, a cohesive bond is formed at the blended interface between the first and second foam layers.

The first and second layers are not limited to foams, and they may be formed from a variety of different materials suitable for padding. For example, the first layer may be foam however the second layer may be a textile.

The method may include the step of laminating an outer layer on the second layer and formed from a hook-receivable material. The outer layer preferably defines an outer surface of the padding and has a thickness substantially less than a thickness of the second layer.

The method may require further laminating an inner layer on the first layer and formed from a compact fabric napped and felted for a smooth surface. The inner layer defines an inner surface of the padding and has a thickness substantially less than a thickness of the first layer. The outer and inner layers may be continuously laminated with the first and second layers or successively bonded. The method may yet further involve the step of attaching a substantially rigid or rigid shell to an inner of the padding, and selectively attach an outer surface of the shell to a segment of a strap.

The numerous advantages, features and functions of the embodiments will become readily apparent and better understood in view of the following description and accompanying drawings. The following description is not intended to limit the pad assembly, but instead merely provides exemplary embodiments for ease of understanding.

BRIEF DESCRIPTION OF THE DRAWINGS

These and other features, aspects, and advantages of the disclosure will become better understood regarding the following description, appended claims, and accompanying drawings.

In the figures, similar elements are provided with similar reference numbers. The drawing figures are not drawn to scale, or proportion, but instead are drawn to provide a better understanding of the components, and are not intended to be limiting in scope, but provide exemplary illustrations.

DETAILED DESCRIPTION OF VARIOUS EMBODIMENTS

Figure 1:
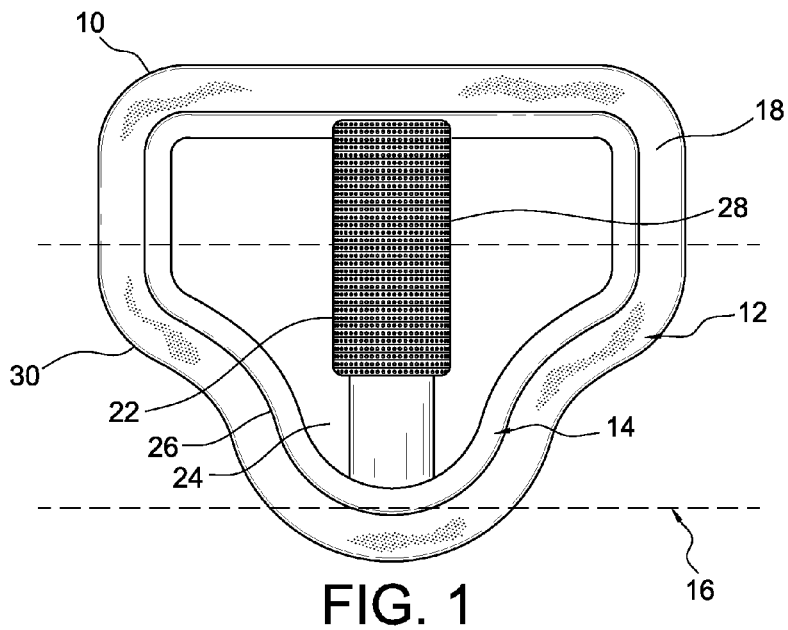
FIG. 1 is a perspective view showing an embodiment of a pad assembly.
Figure 2:
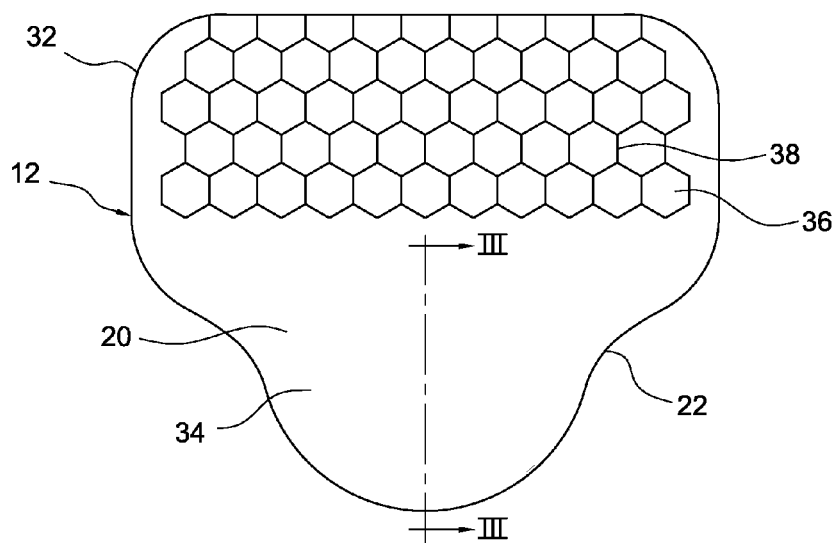
FIG. 2 is a plan view showing an inner surface of padding in the pad assembly of FIG. 1.
Figure 3:
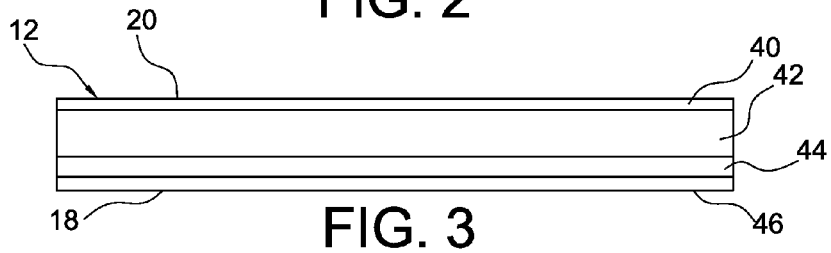
FIG. 3 is cross-sectional view taken along line III-III in FIG. 2.

In observing the embodiment of FIGS. 1-3, the pad assembly 10 includes padding 12 defining inner and outer surfaces 18, 20. The padding 12 includes a first resilient layer 42 accessible from the outer surface 18 and a second layer 44 underlying and bonded and/or laminated to the first layer 42. The first layer 42 defines at least first and second removable sections 36 arranged in a pattern and separated by edge clearances 38, preferably cut from only the first layer 42. Each of the first and second removable sections 36 is tearable from the second layer 44 such that a residual portion 56 of the removable section 36 remains when at least one of the first and second removable sections 36 is removed from the second layer 44.

The pad assembly 10 may also comprises a strap 16 defining a hook-receivable surface material, and a substantially rigid or rigid shell 14 preferably defining an inner fastener 30 defined on an inner surface of the shell 14 and removably securable to the outer surface 20 of the padding 12, and an outer fastener 30 substantially formed on an outer surface of the shell 14 and removably securable to the surface material of the strap 16.

The inner and outer fasteners of the shell may be defined as integrally formed hook elements formed from a same material forming the shell. The integrally formed hook elements are injection molded when the shell is molded to maintain sufficient structural integrity due to repeated removal from the strap and readjustment to appropriate locations for the user's anatomy. Alternative fasteners may be used such as snap fasteners, or other hook material having hook elements bonded to the surfaces of the shell, and therefore the shell is not limited to having injection molded hook elements.

The padding 12 and the shell 14 may each define a similar profile 22, 26. The profile of the padding 12 preferably has a dimension larger than the profile of the shell 14, and is arranged for adapting to anatomy of a user. The padding 12 may have a profile or contour substantially larger than the shell, and a clinician can trim the size of the profile according to the required size of a user. Because of the light construction of the padding, the clinician may trim the profile of the padding without substantial regard to the pattern of the removable portions if a sufficient pressure relief area may be formed with the remaining profile of the padding. The shell may likewise be sufficiently thin or otherwise was trimmed according to the anatomy of the user.

A preferable shape of the padding 12 is shown in FIG. 2, wherein the padding 12 defines an upper portion 32 having a wider width than the lower portion 34. The removable sections 36 may be defined in the upper portion 32 of the padding 12. This shape is adapted for securing against a user's shin or tibia with the upper portion 32 proximate to the knee, and including the removable sections 36 that may be removed to form pressure relief areas corresponding to sutures resulting from an operation.

The shell 14 may define a three-dimensional shape defined by a cross-section such as a generally V-shape. In the depicted example of FIG. 1, the shell 14 preferably includes a generally central bend 28, and the padding is preferably sufficiently flexible to conform to the three-dimensional shape of the shell 14.

The first layer 42 of the padding 12 may be formed from a first foam, such as EVA, and the second layer 44 of the padding 12 is formed from a second foam, such as polyethylene. The second foam 44 may have a greater density or resiliency than the first foam 44 to assure that the first layer 42 tears at or near the interface with the second layer 44 while maintaining the integrity of the second layer 44.

FIG. 3 shows the first layer 42 having a thickness at least double a thickness of the second layer 44 since the first layer 42 forms or takes up mostly the pressure relieving function of the padding 12. Depending on the material used to form the first layer 42, the first layer is not limited to having a double thickness, but may have any suitable thickness permitting it to tear from the second layer while leaving the second layer intact and forming pressure relief areas while maintaining the integrity of the second layer with the residual portion of the first layer.

The padding 12 may further include an inner layer 40 bonded on the first layer 42 and formed from a compact fabric napped and felted for a smooth surface. The inner layer 40 may define the entire inner surface 20 of the padding 12 and have a thickness substantially less than a thickness of the first layer 42. The inner layer 40 is preferably provided only as a skin interface and is not intended to structurally impact the tearability of the removable sections or inhibit flexibility of the padding 12.

The padding 12 may further include an outer layer 46 bonded on the second layer 44 and formed from a hook-receivable material. The thickness of the outer layer 46 is thickness substantially less than a thickness of the second layer 44. The outer layer 46 may define the entire outer surface 18 of the padding 12.

Figure 4:
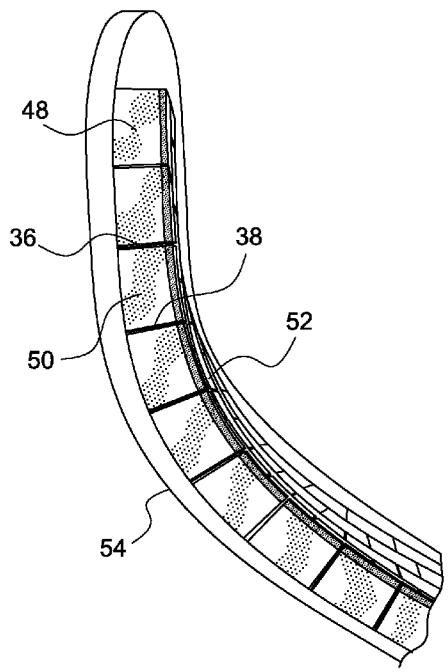
FIG. 4 is a perspective view showing the padding of FIG. 2 in a bent configuration with removable sections intact with the padding.
Figure 5:
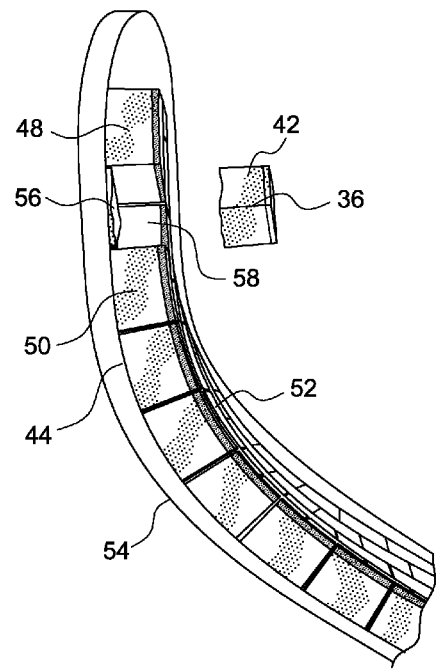
FIG. 5 is a perspective view of the padding of FIG. 4 with a removable section detached from the padding and leaving a residual portion on the padding.

As in FIGS. 4 and 5, the first layer 42 forms the residual portion 56, and a void 58 is formed thereabove to form at least part of the pressure relief area. Edge clearances 38 are preferably formed through an entirety of the thickness of the first layer 42, and the removable section 56 defines a thickness short of the entire thickness of the first layer.

The padding 12 is preferably flexible, as shown by inner and outer bends 52, 54 in FIGS. 4 and 5. The flexibility of the padding enables the padding to correspond to both the shape of the shell and the anatomy of the user. The removable sections are preferably formed so as not to inhibit the flexibility of the padding 12, enabling the padding to be used for a variety of anatomies. The padding 12 can be formed irrespective of intended locations for application, and the removable sections can be formed across the entire padding.

Because of the low-cost and simplicity of the padding, portions of the padding can be trimmed away without impeding the function of the padding and may be trimmed irrespective of the pattern of the removable sections since they are preferably small in area. The removable sections may be formed from a variety of shapes and are not limited to the hexagonal shapes depicted, and may have shapes defining squares, rectangles or other suitable shapes.

Figure 6:
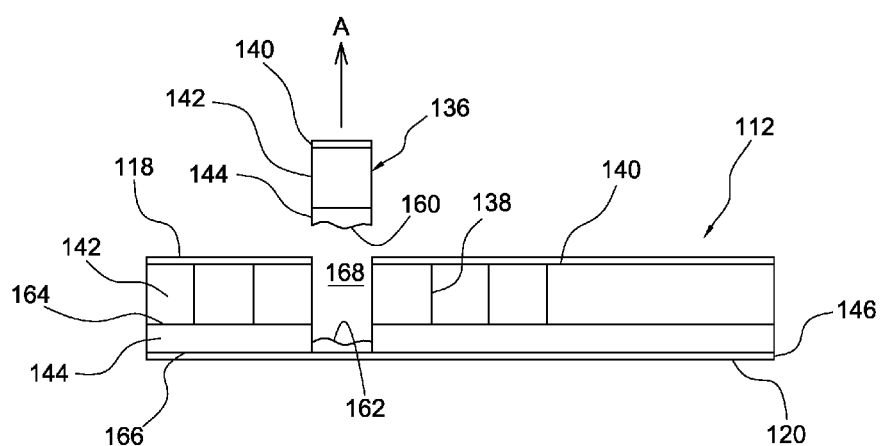
FIG. 6 is a perspective side view of another embodiment of the padding.

In observing FIG. 6, another embodiment of the padding 112 is disclosed wherein a portion of the second layer 144 is stripped away with the first layer 142 when a removable section 136 is removed from the padding 112, as exemplified by the direction A. It will be understood the removable section 136 is not limited to being removed in the direction A but rather any direction suitable for tearing or severing the removable section 136 from the padding 112.

As with the embodiment of FIGS. 2 and 3, the padding 112 includes inner and outer surfaces 118, 120, and inner and outer layers 140, 146 secured to the first and second layers 142, 144 respectively. In this embodiment, a blended interface 164 exists between the first and second layers 142, 144 wherein material from the first and second layers 142, 144 blends into one another chemically and/or mechanically. The blended interface 164 is sufficiently strong and the material forming the second layer 144 is preferably weaker than the material forming the first layer 142 such that removable section 136 preferably tears away from the second layer 144 rather than the first layer 142.

The removable section 136 forms a severed lower portion 160 including some of the second layer when removed from the padding 112. The residual portion 162 defines an edge of the second layer 144, and is defined below the areas of the second layer 144 at the blended interface 164 at intact areas of the padding 112. The residual portion 162 is defined below the blended interface 164 since the chemical and/or mechanical bond between the first and second layers 142, 144 is sufficiently strong to withstand tearing and rather the second layer 144 serves as a weak point facilitating separation of the removable portion 136 from the padding 112.

The interface 166 between the outer layer 146 and second layer 144 is sufficiently strong to prevent tearing of the outer layer 146 when the removable section 136 is separated from the padding 112. Indeed, it is preferably that the residual portion 162 has a sufficient collective height since the upper profile of the residual portion may vary in height, as evidenced by FIG. 6, to maintain structural integrity below the void or the pressure relief area 168 formed by displacement of the removable section 136. The removable section 136 may be discarded after it is removed from the padding 112 since it is of no longer of use.

It will be understood that the embodiments described herein require tearing of the removable sections rather than peeling or detaching (as in hook and loop, adhesive or other fastening means). Intentional weak points are formed by selection of the second layer and are intended to facilitate tearing as the padding of the disclosure is not intended to be reconfigurable but rather low-cost yet effective in forming pressure relief areas.

A variety of methods may be employed for forming the padding. The layers 40, 42, 44 and 46 may be bonded or laminated to one another so they are permanently bonded to one another; the layers will not easily separate from one another and will tear without cleanly removing the layers from one another, as evidence by FIG. 6.

In a preferred method of securing the first and second layers to one another, flame lamination is used to create the blended interface. Flame lamination involves passing the first layer through a controlled flame changing the surface of the first layer, such as when it is foam, to a molten state. The second layer is then brought into direct contact with the molten surface of the first layer under controlled tension and pressure, such as at a nip point. As the molten surfaces rapidly cool, a cohesive bond is formed at the interface between the first and second layer thereby forming the blended interface which chemically and mechanically bonds the first and second layers to one another. There are many factors that control the amount of bond strength achieved between the foam and the substrate including the speed and distance at which the foam passes through the controlled flame.

The first and second layers are not limited to foams, and they may be formed from a variety of different materials suitable for padding. For example, the first layer may be foam however the second layer may be a textile.

In alternative embodiments, the first and second layers may be bonded by other means such as solvent-based adhesive lamination, thermoplastic adhesive lamination, solvent and water-based coating, heat sealing, and other known methods to assure a bond between the first and second layers.

The removable sections may be die cut to form a plurality of removable sections through a thickness of the first layer by forming a plurality of edge clearances between each of the removable sections. The edge clearances are preferably narrow in width so as to not hinder the structural integrity of the padding, but permits easy tearing of the removable sections away from the second layer.

In conclusion, several illustrative embodiments have been discussed hereinabove. It will be understood that various changes and modifications may be made without departing from the spirit and scope of the disclosure. The disclosure is not limited to the precise embodiments described hereinabove.

The invention claimed is:

1. A pad assembly for an orthopedic device, comprising:
a padding defining first and second surfaces, the padding including a first layer being resilient and accessible from the first surface and a second layer being resilient and underlying and secured to the first layer, the first and second layers of padding being laminated to one another at an interface;
wherein first and second removable sections are both formed from at least one of the first and second layers of the padding, and are arranged in a pattern and separated by edge clearances, each of the first and second removable sections being tearable from only the first layer of the padding such that a residual portion of the first layer remains secured on the second layer when at least one of the first and second removable sections is removed from the padding;

wherein the interface between the first and second layers of the padding is more resistant to tearing than the first and second layers of the padding such that the interface remains intact when one of the first and second removable sections is removed from the padding.

2. The pad assembly of claim 1, further comprising:
a strap defining surface material;
a substantially rigid or rigid shell defining an inner fastener on an inner surface removably securable to the second surface of the padding, and an outer fastener on an outer surface removably securable to the surface material of the strap.

3. The pad assembly of claim 2, wherein the padding and the shell each define a similar profile, the profile of the padding having a dimension larger than the profile of the shell.

4. The pad assembly of claim 2, wherein the inner and outer fasteners of the shell are defined as integrally formed hook elements formed from a same material forming the shell.

5. The pad assembly of claim 2, wherein the shell defines a three-dimensional shape defined by a V-shape cross-section including a central bend, the padding conforming to the three-dimensional shape of the shell.

6. The pad assembly of claim 2, wherein the padding and the shell have peripheries arranged for trimming modification.

7. The pad assembly of claim 1, wherein the padding defines a lower portion having a narrower width than an upper portion.

8. The pad assembly of claim 7, wherein the first and second removable sections are defined in the upper portion of the padding.

9. The pad assembly of claim 1, wherein the padding has a periphery arranged for trimming and modification.

10. The pad assembly of claim 1, wherein the edge clearance is defined through an entirety of the thickness of the first layer, and wherein the removable section defines a thickness short of the entire thickness of the first layer.

11. The pad assembly of claim 1, wherein the first layer of the padding is formed from a first foam and the second layer of the padding is formed from a second foam, the second foam having resiliency greater than the first foam.

12. The pad assembly of claim 1, wherein the first layer of the padding is formed from a first foam and the second layer of the padding is formed from a second foam, the second foam being weaker than the first foam, and serves as a weak point for the removable section so as to yield to tearing when a force is used to pull or tear the removable section away from the padding.

13. The pad assembly of claim 1, wherein a blended interface is defined along the first and second layers such that they are chemically and/or mechanically bonded to one another, the blended interface consisting a blend of materials of the first and second layer at the interface, and the removable section is torn away from the second layer of the padding below the blended interface.

14. The pad assembly of claim 1, wherein the first layer has a thickness at least double a thickness of the second layer.

15. The pad assembly of claim 1, wherein the residual portion of the first layer extends over an entirety of a portion of the second layer underlying from which the removable section is removed.

16. A method for forming a pad assembly having permanent pressure relief areas, comprising:
laminating a first foam layer onto a second foam layer so as to form a blended interface therebetween;
die cutting a plurality of removable sections through a thickness of the first foam layer by forming a plurality of edge clearances between each of the removable sections;
laminating an inner layer on the first layer and formed from a compact fabric napped and felted for a smooth surface, the inner layer defining an inner surface of the padding and having a thickness substantially less than a thickness of the first layer.

17. The method of claim 16, wherein the die cut is formed through only the thickness of the first foam layer and terminates short of the blended interface.

18. The method of claim 16, further comprising the step of removing at least one of the plurality of removable sections corresponding to a sensitive area of a user, wherein a residual portion of the first layer remains on the second layer after the at least one removable section is removed from the pad assembly.

19. The method of claim 16, further comprising the step of laminating an outer layer on the second layer and formed from a hook-receivable material, the outer layer defines an outer surface of the padding and having a thickness substantially less than a thickness of the second layer.

20. A pad assembly for an orthopedic device, comprising:
a padding defining first and second surfaces, the padding including a first layer being resilient and accessible from the first surface and a second layer being resilient and underlying and secured to the first layer,
wherein first and second removable sections are both formed from at least one of the first and second layers of the padding, and are arranged in a pattern and separated by edge clearances, each of the first and second removable sections being tearable from only the first layer of the padding such that a residual portion of the first layer remains secured on the second layer when at least one of the first and second removable sections is removed from the padding;
wherein the first layer of the padding is formed from a first foam and the second layer of the padding is formed from a second foam, the second foam being weaker than the first foam, and serves as a weak point for the removable section so as to yield to tearing when a force is used to pull or tear the removable section away from the padding;
wherein an interface is defined along the first and second layers such that they are chemically and/or mechanically bonded to one another, and the interface is more tear-resistant than the first and second layers of the padding such that the interface remains intact when one of the first and second removable sections is removed from the padding.

* * * * *